United States Patent [19]

Slichter et al.

[11] Patent Number: 4,998,931

[45] Date of Patent: Mar. 12, 1991

[54] METHOD OF REDUCING IMMUNOGENICITY AND INDUCING IMMUNOLOGIC TOLERANCE

[75] Inventors: Sherrill J. Slichter, Vashon Island; H. Joachim Deeg, Seattle, both of Wash.

[73] Assignees: Puget Sound Blood Center; Fred Hutchinson Cancer Research Center, both of Seattle, Wash.

[21] Appl. No.: 290,856

[22] Filed: Dec. 21, 1988

Related U.S. Application Data

[63] Continuation of Ser. No. 58,599, Jun. 3, 1987, abandoned, which is a continuation of Ser. No. 752,452, Jul. 5, 1985, abandoned.

[51] Int. Cl.⁵ .......................... A61N 1/30; A61F 2/04
[52] U.S. Cl. ..................................... 604/20; 128/898; 600/36
[58] Field of Search ............... 604/4, 20, 28; 128/395, 128/DIG. 3, 897, 898; 600/36

[56] References Cited

U.S. PATENT DOCUMENTS

| | | | |
|---|---|---|---|
| 4,321,918 | 3/1982 | Clark, II | 604/20 |
| 4,321,919 | 3/1982 | Edelson | 604/20 |
| 4,428,744 | 1/1984 | Edelson | 604/20 |
| 4,464,166 | 8/1984 | Edelson | 604/20 |
| 4,608,255 | 8/1986 | Kahn et al. | 424/101 |
| 4,861,704 | 8/1989 | Reemtsma et al. | 435/1 |

OTHER PUBLICATIONS

M. A. Hardy, H. T. Lau, C. Weber, and K. Reemtsma, "Pancreatic Islet Transplantation: Immuno-Alteration with Ultraviolet Irradiation", *World J. Surg.*, 8(2):207–213, Apr., 1984.

H. Lau, K. Reemtsma, and M. A. Hardy, "The Use of Direct Ultraviolet Irradiation and Cyclosporine in Facilitating Indefinite Pancreatic Islet of Allograft Acceptance", *Transplantation* 38(6):566–569, Dec. 1984.

H. Lau, K. Reemtsma, and M. A. Hardy, "Prolongation of Rat Islet Allograft Survival by Direct Ultraviolet Irradiation of the Graft", *Science* 223:607–609, Feb. 10, 1984.

J. D. Balshi, M.D., J. W. Francford, M.D., and L. J. Perloff, M.D., "The Influence of Ultraviolet Irradiation on the Blood Transfusion Effect", *Surgery*, 98(2):243–250, Aug., 1985.

M. A. Hardy, H. Lau, and K. Reemtsma, "Prolongation of Rat Islet Allografts with the use of Ultraviolet Irradiation, Without Immunosuppression", *Transplantation Proceedings*, 16(3):865–869, 1984.

M. A. Hardy, H. Lau, C. Weber, and K. Reemtsma, "Induction of Graft Acceptance by Ultraviolet Irradiation of Donor Tissue", *Ann. Surg.*, 200(4):441–450, 1984.

H. Lau et al., *Eur. Sur. Res.*, 16(suppl. 1):42–43, 1984.

H. Lau et al., "Pancreatic Islet Allograft Prolongation by Donor-Specific Blood Transfusions Treated with Ultraviolet Irradiation", *Science*, 221:754–755, 1983.

R. D. Granstein, "Epidermal I-J-Bearing Cells are Responsible for Transferable Suppressor Cell Generation After Immunization of Mice with Ultraviolet Radiation-Treated Epidermal Cells", *J. of Investigative Dermatology*, 84(3):206–209, 1985.

M. L. Kripke, "Immunological Unresponsiveness Induced by Ultraviolet Radiation", Immunological Reviews 80:86–101, 1984.

L. M. Slater et al., "Dissimilar Effects of Ultraviolet Light on HLA-D and HLA-DR Antigens", *Tissue Antigens*, 15:431–435, 1980.

R. M. Steinman and M. C. Nussenzweig, "Dentritic Cells: Features and Functions", *Immunological Rev.*, 53:127–147, 1980.

S. J. Slichter, H. J. Deeg, M. Kennedy, "Prevention of Platelet (PLT) Alloimmunizations: Use of Cyclosporine-Loaded (C-L) or UV Irradiated Donor Plts.", Am. Soc. of Hematology, 26 Annual Meeting, Dec. 1–4, 1984.

*Primary Examiner*—C. Fred Rosenbaum
*Assistant Examiner*—Sharon Rose
*Attorney, Agent, or Firm*—Seed and Berry

[57] ABSTRACT

The immunogenicity of transfused or transplanted, allogeneic tissue is reduced by either directly exposing the tissue to ultraviolet (UV) irradiation prior to administering the tissue to the recipient or by inducing a state of tolerance in the recipient to non-UV or UV-irradiated allogeneic tissue by prior exposure to UV-irradiated allogeneic tissue.

13 Claims, No Drawings

METHOD OF REDUCING IMMUNOGENICITY AND INDUCING IMMUNOLOGIC TOLERANCE

CROSS REFERENCE TO RELATED APPLICATION

This application is a continuation of U.S. patent application Ser. No. 058,599, filed June 3, 1987, now abandoned under C.F.R. § 1.62, which was a continuation of U.S. patent application Ser. No. 752,452, filed July 5, 1985, now abandoned.

FIELD OF THE INVENTION

The present invention relates to methods of reducing the immunogenicity of allogeneic tissues such as blood transfusions and allografts and to methods of inducing immunologic tolerance to allogeneic tissues in putative recipients.

BACKGROUND OF THE INVENTION

Patients with a variety of disorders receive intermittent or chronic transfusion support or require tissue grafting to replace a defective organ. For individuals requiring transfusion support, they have either a genetic or acquired deficiency of one or more blood components that require replacement therapy. Many different products prepared from blood are available for transfusion, including both cellular and plasma components. However, repeated exposure to blood products often results in recipient recognition of the foreign transfused antigens. Such immune recognition of the foreign antigens results in a failure to achieve a benefit from the transfusion and in some circumstances may even cause a transfusion reaction with adverse consequences to the recipient.

Several approaches have been used to either prevent or delay alloimmunization. The majority of the techniques involve giving immunosuppressive therapy to the transfusion recipient to prevent recognition of the transfused foreign antigens. Such immunosuppressive therapy is often inadequate to suppress the recognition process resulting in alloimmunization in spite of the treatment. Furthermore, the immunosuppressive therapy may have undesirable side effects including organ toxicity and immunosuppression of desirable responses such as recognition and destruction of pathogenic bacteria.

Once an immune response to foreign antigens has occurred, there is little evidence that any immunosuppressive therapy is beneficial. Continued adequate transfusion support is possible only if antigen matching between donor and recipient is achieved. Often a matched donor is not available or for some transfusion products so little is known about the antigen systems involved in the immune response that laboratory methods are not available to appropriately select a matched donor.

An alternative approach to preventing alloimmunization, other than immunosuppressing the recipient, is to reduce the immunogenicity of the transfused product. As al transfused blood products are immunogenic and will eventually induce an immune response in most transfused recipients, any procedure that can prevent or at least delay immunization is beneficial. Selecting only antigen compatible donors beginning with the first transfusion is possible in some circumstances but for the majority of patients not enough donors are available to continue this process or a matching procedure does not exist.

For organ grafting, because there is persistent exposure to foreign tissue antigens, eventual rejection of the grafted tissue occurs. To prevent graft rejection several approaches have been used: recipient immunosuppression, matching tissue antigens of donor and recipient, reducing the immunogenicity of the grafted tissue, or inducing a state of tolerance in the recipient to the foreign antigens of the graft. Furthermore, depending on the tissue being grafted different approaches may be required to achieve a successful graft and combined therapies may be additive in their beneficial effects. For example, in bone marrow transplantation massive doses of chemo-radiotherapy are given to the recipient to destroy the recipient's autologous marrow and to induce immunosuppression to allow engraftment of the donor marrow. Even better results are obtained if marrow donor and recipient are related and well-matched for the major histocompatibility antigen system (HLA). Although post-marrow grafting immunosuppression is usually given, it is for only a limited time.

In contrast, for kidney grafting lesser degrees of immunosuppressive therapy are required to avoid unacceptable marrow and gastrointestinal toxicity. Furthermore, continuous post-grafting immunosuppression is required. Often a related kidney donor is not available, and lesser degrees of HLA matching between donor and recipient are more often accepted than for bone marrow transplantation.

Another major difference between these two types of tissue grafting are the effects of prior transfusions on engraftment. For kidney graft recipients, prior transfusions, particularly from the intended kidney donor, are beneficial apparently by inducing some degree of tolerance to the subsequent kidney graft. However, prior blood transfusions before marrow grafting, especially if the blood has come from the intended marrow donor, markedly increases the risk of graft rejection. Thus, although there are similarities in procedures to enhance organ grafts (immunosuppression and donor-recipient HLA matching) there are clear differences in (1) the amounts, type, and duration of immunosuppression required; (2) the acceptance of non-HLA identity between organ donor and recipient; and, (3) the effects of prior transfusions on enhancing or impairing a subsequent organ graft. Furthermore, even the best combined therapies are not always successful in ensuring a successful organ graft, and there may be substantial toxicities associated with the therapies being used.

Besides using HLA matching and recipient immunosuppression, efforts to directly reduce immunogenicity of the engrafted tissue or to enduce tolerance in the recipient, other than by prior blood transfusions in kidney recipients, have been limited. In bone marrow transplantation efforts to purify or enrich the marrow graft for stem cells and eliminate T-lymphocytes that may be responsible for graft vs. host disease (a post-grafting complication) have often resulted in a transplanted marrow that has failed to engraft. Some investigators have stored r cultured the graft in vitro prior to transplantation (skin grafting) to facilitate engraftment. Most of these latter methods to enhance organ grafting have had limited success.

It would be advantageous to avoid immune recognition by the recipient of incompatible donor antigens and the consequent destruction of allogeneic tissue following transfusion or transplantation.

SUMMARY OF THE INVENTION

Pursuant to this invention the immunogenicity of transfused or transplanted, allogeneic tissue is reduced by either directly exposing the tissue to ultraviolet (UV) irradiation prior to administering the tissue to the recipient or by inducing a state of tolerance in the recipient to non-UV or UV-irradiated allogeneic tissue by prior exposure to UV-irradiated allogeneic tissue.

In the first instance, the immunogenicity of the allogeneic tissue, for example blood products intended for transfusion, is reduced by subjecting the allogeneic tissue to a total UV exposure that does not substantially interfere with the viability or physiological function of the allogeneic tissue. The threshold exposure of UV irradiation at which substantial interference with viability or physiological function occurs can be determined with reference to tissue-specific parameters of viability and function for unmanipulated, non-UV irradiated tissue using standard laboratory testing protocols.

For some transplanted tissues, a UV dose effective in reducing immunogenicity may be impossible to administer due to the bulk nature of the engrafting tissue, e.g., cardiac and kidney grafts, recognizing the low penetrance of UV irradiation. Alternatively, for some tissues the threshold exposure at which biologic activity is substantially unimpaired may be too low to prevent immune recognition when the tissue is administered to the recipient. For these circumstances, a UV-irradiated tolerizing tissue can be administered to the recipient prior to or concurrent with the administration of the engrafting tissue. For this purpose the dose of UV irradiation need not necessarily maintain the biologic activity of the UV-irradiated tissue being used to induce tolerance. Nor must the tolerizing and engrafting tissues be histologically identical. The tolerizing and engrafting tissues can be from the same, related, or unrelated donor(s), i.e., including immunologically responsive donor/recipient combinations.

DETAILED DESCRIPTION OF THE PREFERRED EMBODIMENT

Pursuant to this invention the immunogenicity of transfused or transplanted, allogeneic tissue is reduced by either directly exposing the tissue to ultraviolet (UV) irradiation prior to administering the tissue to the recipient or by inducing a state of tolerance in the recipient to non-UV or UV-irradiated allogeneic tissue by prior exposure to UV-irradiated allogeneic tissue.

In the first instance, the immunogenicity of the allogeneic tissue, for example blood products intended for transfusion, is reduced by subjecting the allogeneic tissue to a total UV exposure that does not substantially interfere with the viability or physiological function of the allogeneic tissue. The threshold exposure of UV irradiation at which substantial interference with viability or physiological function occurs can be determined with reference to tissue-specific parameters of viability and function for unmanipulated, non-UV irradiated tissue using standard laboratory testing protocols.

For example, red blood cells and platelets can be subjected to total exposure of UV irradiation (200 nm to 330 nm) on the order of 1350 and 12 to 36 $mJ/cm^2$, respectively, without substantial interference with their viability or physiological function. Moreover, subjecting whole blood or platelet suspensions to ultraviolet radiation a the respectively stated exposures causes a significant reduction in their immunogenicity.

For some transplanted tissues, a UV dose effective in reducing immunogenicity may be impossible to administer due to the bulk nature of the engrafting tissue, e.g., cardiac and kidney grafts, recognizing the low penetrance of UV irradiation. Alternatively, for some tissues the threshold exposure at which biologic activity is substantially unimpaired may be too low to prevent immune recognition when the tissue is administered to the recipient. For these circumstances, a UV-irradiated tolerizing tissue can be administered to the recipient prior to or concurrent with the administration of the engrafting tissue.

For the purpose of inducing tolerance the dose of UV irradiation need not necessarily maintain the biologic activity of the UV-irradiated tissue being used to induce tolerance. Nor must the tolerizing and engrafting tissues be histologically identical, or from the same or related donors.

The following Examples are presented to illustrate the advantages of the present invention and to assist one of ordinary skill in making and using the same. The following Examples are not intended in any other way to otherwise limit the scope of the disclosure or the protection granted by Letters Patent hereon.

EXAMPLE 1

Platelet transfusion experiments were performed between unrelated donor-recipient dog pairs that were randomly selected from a pool of animals. The experimental design involved preparing a platelet concentrate from 50 ml of blood drawn from a donor animal and radiolabelling the donor's platelets with $^{51}$Chromium as described in J. Immunol. 117:143–150, 1976. After transfusion of the radiolabelled donor dog's platelets into a recipient, serial blood samples were drawn from the recipient to determine the disappearance rate of the donor's platelets from the recipient's circulation. The normal survival of autologous radiolabelled platelets in the dog is 5.1 days ±0.4. If there were no circulating radiolabelled donor platelets in the recipient at 24 hours post-transfusion, the animal was considered to be alloimmunized to the donor's platelets.

In 21 recipients, weekly transfusion of a single, unrelated donor's platelets resulted in immunization in 20 recipients (95%) after an average of 3.1±0.7 transfusions (range 2–12). Of these non-irradiated control transfusion recipients 18/21 (86%) were immunized by eight transfusions.

In an effort to prevent immune recognition of the transfused platelets, 9 randomly selected donor-recipient pairs were transfused with UV-irradiated donor platelets. Before these transfusion studies were begun, 14 animals had their autologous platelets UV-irradiated and after radiolabelling these platelets were returned to the donor. These experiments showed that UV-irradiation doses of greater than 600 uwatts/$cm^2$ for more than 10 minutes (total dose of 360 $mJ/cm^2$) resulted in loss of platelet viability as documented by an absent or reduced autologous platelet survival determination. Based on these autologous studies, for the experimental paired donor-recipient transfusion studies we selected and used doses of UV irradiation that did not produce loss of platelet viability.

Specifically, 9 recipient animals received $^{51}$Cr radiolabelled donor platelets that had been exposed to 200, 400, or 600 uwatts of UV irradiation/$cm^2$ for one minute delivered by a germocidal lamp (total dose of 12, 24, and 36 $mJ/cm^2$, respectively). The platelets were exposed to the UV irradiation by placing them to a depth of about 1-2 cm in an open Petri dish which was continually agitated throughout the UV exposure. The same randomly-selected donor-recipient pairs were used for a minimum of eight weekly transfusions. Only 2/9 (22%) of the recipient dogs who received UV-irradiated donor platelets became immunized.

Next, in the 7 non-immunized recipients (after the eight weeks of UV-irradiated platelets had been given) an additional 12 weeks of non-irradiated platelet transfusions from the same donor were given. Only 2/7 (29%) of these recipients were able to recognize the UV non-irradiated platelets from their donor. However, if non-UV irradiated platelets from a new donor were subsequently given to the 5 recipients who had failed to recognize non-UV irradiated platelets from their original donor, 2 of these recipients (40%) failed to become immunized to these new donor's platelets after 8 transfusions. The other 3 were immunized by the new donor's platelets by 1,1, and 9 transfusions, respectively. This data demonstrates that tolerance to non-UV irradiated transfused donor platelets was induced in these recipients by prior transfusions of UV-irradiated platelets.

EXAMPLE 2

In these experiments using a canine model we show that exposure of blood to ultraviolet light before transfusion prevents immunization and allows for subsequent marrow engraftment.

Normal dogs given 9.2 Gy of total body irradiation and bone marrow transplants from a DLA (major histocompatibility complex)-identical littermate donors generally achieve sustained engraftment and become long-term survivors. However, if recipient dogs are transfused with whole blood from the marrow donor before transplantation the marrow graft is always rejected and the recipient dogs uniformly die with marrow aplasia. Such graft rejections are apparently the result of transfusion-induced sensitization of the recipient against minor (non-DLA) histocompatibility antigens of the donor.

In this Example, normal dogs were given 9.2 Gy total body irradiation, hemopoietic marrow infusion from DLA identical littermates, and post-transplant conditioning as described in Blood 54:477, 1979. Prior to marrow grafting recipients were given 3 transfusions on days 24, 17, and 10 before transplantation. The transfusions consisted of either unmanipulated or UV-irradiated or sham-irradiated whole blood from the marrow donor. The following procedure was used. Whole blood (50 ml/transfusion) was obtained from a donor Beagle dog by venipuncture into syringes containing preservative-free heparin to prevent coagulation. The blood was then diluted 1:1.5 with Waymouth's Minimal Medium. Aliquots of 7.5 ml were placed in 10 plastic dishes (Falcon #3003), resulting in a layer of 1.5 mm thickness in each dish. The uncovered plates, placed on a shaker platform to assure continual mixing of the blood, were then exposed for 30 minutes to UV irradiation (220-300 nm wavelength) from a germicidal lamp (General Electrics) at an intensity of 750 uW/cm$^2$ (total exposure 1350 mJ/cm$^2$) as determined with a Black Ray shortwave UV meter (U.V. Products). Cells were then quantitatively recovered from the dishes, collected into syringes and injected into a recipient dog. Sham-irradiated blood was handled in an identical fashion except that it was exposed to visible light instead of UV light.

TABLE 1 shows the results of these experiments.

TABLE 1

| Group | Transfusions | No. of Dogs Studied | with graft rejection | with sustained graft | Incidence of sustained graft |
|---|---|---|---|---|---|
| 6 | None | 60 | 1 | 59 | 98% |
| 7 | whole blood, unmanipulated | 21 | 21 | 0 | 0% |
| 8 | whole blood, UV-irradiated | 10 | 0 | 10 | 100% |
| 9 | whole blood, sham-irradiated | 4 | 4 | 0 | 0% |

The majority of the dogs in Groups 6 and 7 were included in the above-cited previous report. Of the ten dogs of Group 8 that sustained the graft, three died with septicemia at 8, 9 and 13 days, respectively. Engraftment was documented by rising granulocyte counts following the post-irradiation nadir and by the presence of erythroid and myeloid precursor cells (total cellularity 10-25% of normal) on marrow samples obtained at autopsy. The other seven dogs are surviving after more than 100 days; in these sustained engraftment was documented by the presence of the donor sex karyotype in all metaphase spreads from bone marrow and peripheral blood (four dogs) or the conversion to the donor erythrocyte antigen pattern (three dogs). Dogs of group 9 died on days 10, 11, 11, and 13, respectively, with septicemia. Marrow cellularity at autopsy was less than 5% in all of these dogs. Cells were composed of plasma cells and reticulum cells; hemopoietic precursor cells were absent.

All of the dogs that were given transfusions of UV-exposed blood prior to marrow transplantation sustained engraftment nd behaved like dogs not given any transfusions before transplantation. In contrast, all of the control dogs, transfused before transplantation with blood exposed to light in the visible range rather than the UV range, failed to achieve substantial engraftment and died with bone marrow aplasia, similar to the dogs given transfusions of unmanipulated whole blood. Thus, exposure of blood to UV light appears to abrogate the sensitizing ability of blood and allows for subsequent successful engraftment.

In patients undergoing marrow transplantation for various diseases, especially severe aplastic anemia, exposure to transfusion products before marrow transplantation as in our dog model leads to a significant risk of subsequent marrow graft rejection. While patients who are untransfused at the time of marrow transplantation usually achieve sustained engraftment and become healthy survivors, patients who have been given transfusions before transplantation have been reported in previous studies to have an incidence of graft rejection as high as 60%. Since graft rejection is usually not compatible with the patient's survival, it is highly desirable to prevent sensitization of the patient before transplantation. The method described here provides such an approach. Furthermore, it is contemplated that this method may result in tolerance of other transplants, e.g., kidney or heart, as well.

EXAMPLE 3

UV exposure as described in Example 2 is compatible with useful red cell transfusion support. In one dog we measured the survival of UV-exposed Chromium-51 labelled red blood cells according to standard techniques. The $T_{\frac{1}{2}}$ was 17 days, which compares to a range of 17-24 days measured in dogs given unmanipulated transfusions.

While the present invention has been described in conjunction with a preferred embodiment and illustrative examples, one of ordinary skill after reading the foregoing specification will be able to effect various changes, substitutions of equivalents, and other alterations to the methods set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A method of reducing the immunogenicity of blood or blood products in vitro, comprising:
   exposing the blood or blood products to a source of UV irradiation sufficient to reduce the immunogenicity of the blood or blood products without substantially interfering with the viability or physiological function of the blood or blood products.

2. The method of claim 1 wherein the blood or blood product is selected from the group consisting of whole blood, red cells, white cells, platelets and plasma constituents.

3. The method of claim 1 wherein the blood product is a non-platelet blood product and wherein the UV irradiation results in an exposure of from about 120 $J/m^2$ to about 13,500 $J/m^2$.

4. The method of claim 2 wherein the blood product is platelets and the UV irradiation results in an exposure of from about 120 $J/m^2$ to about 360 $J/m^2$.

5. The method of claim 2 wherein the blood product is red blood cells and the UV irradiation results in an exposure of approximately 13,500 $J/m^2$.

6. A method of reducing the immunogenicity of blood in vitro, comprising:
   exposing the blood to a source of UV irradiation sufficient to reduce the immunogenicity of the blood within an immunologically responsive recipient.

7. The method of claim 6 wherein the UV irradiation results in an exposure of from about 120 $J/m^2$ to about 13,500 $J/m^2$.

8. The method of claim 6 wherein the dose of UV irradiation does not substantially interfere with the viability or physiological function of the transfused or transplanted tissue.

9. A method of inducing immunologic tolerance to transfused or transplanted tissue, comprising:
   exposing the transfused or transplanted tissue to a source of UV irradiation sufficient to induce immunologic tolerance to a subsequent transfusion or transplantation within an immunologically responsive recipient.

10. The method of claim 9 wherein the transfused or transplanted tissue is selected from the group consisting of bone marrow, skin, pancreas, bone, liver, heart/lung, kidney and cornea.

11. The method of claim 9 wherein said transfused or transplanted tissue is blood.

12. The method of claim 9 wherein the UV irradiation results in an exposure of from about 120 $J/m^2$ to about 13,500 $J/m^2$.

13. The method of claim 9 wherein the dose of UV irr

* * * * *

UNITED STATES PATENT AND TRADEMARK OFFICE
CERTIFICATE OF CORRECTION

PATENT NO. : 4,998,931

DATED : March 12, 1991

INVENTOR(S) : Sherrill J. Slichter; H. Joachim Deeg

It is certified that error appears in the above-identified patent and that said Letters Patent is hereby corrected as shown below:

In column 6, line 48, please delete "nd" and substitute therefor -- and --.

In column 8, claim 13, line 39, after "UV" please delete "irr" and substitute therefor -- irradiation does not substantially interfere with the viability or physiological function of the transfused or transplanted tissue. --.

Signed and Sealed this

Twenty-second Day of September, 1992

Attest:

DOUGLAS B. COMER

*Attesting Officer*   *Acting Commissioner of Patents and Trademarks*